United States Patent
Li et al.

(10) Patent No.: US 6,696,296 B2
(45) Date of Patent: Feb. 24, 2004

(54) LEAK DETECTOR FOR SEALED OPTICAL DEVICES

(75) Inventors: Jason Li, Union City, CA (US); Steven Guoxin Zhu, Fremont, CA (US)

(73) Assignee: Oplink Communications, Inc., San Jose, CA (US)

( * ) Notice: Subject to any disclaimer, the term of this patent is extended or adjusted under 35 U.S.C. 154(b) by 395 days.

(21) Appl. No.: 09/800,399

(22) Filed: Mar. 5, 2001

(65) Prior Publication Data

US 2002/0142469 A1 Oct. 3, 2002

(51) Int. Cl.$^7$ .............................................. G01N 31/00
(52) U.S. Cl. ............................. 436/3; 436/1; 436/164; 116/4; 73/40.7; 73/40
(58) Field of Search .................. 116/4; 73/40, 40.5 R, 73/40.5 A, 40.7, 49.3; 436/1, 3, 164

(56) References Cited

U.S. PATENT DOCUMENTS 3,729,983 A * 5/1973 Coppens ..................... 73/40.7
3,987,664 A * 10/1976 Hass et al. ................... 73/49.2

* cited by examiner

Primary Examiner—Lyle A. Alexander
(74) Attorney, Agent, or Firm—Fish & Richardson P.C.

(57) ABSTRACT

This invention discloses a method for detecting a leak from a sealed optical device. The method includes steps of: A) injecting a target gas with no performance interference to the sealed optical device for leak detection followed by sealing the sealed optical device. B) placing the sealed device in a leak testing chamber and measuring a background level of the target gas in the leak testing chamber. C) heating the sealed device to a gas-expelling temperature for expelling the target gas from the leak in the sealed optical device. And, D) detecting the target gas in a one-part-per million (PPM) range in the leak-detecting chamber for an comparing with the background level of the target gas for determining the leak in the sealed optical device.

26 Claims, 4 Drawing Sheets

LEAK DETECTOR FOR SEALED OPTICAL DEVICES

FIELD OF THE INVENTION

The present invention relates generally to apparatuses and method for leak detection. More particularly, this invention relates to apparatuses and methods for leakage detection for sealed optical devices.

BACKGROUND OF THE INVENTION

Manufacturers of fiber optical components are often encountered with the difficult tasks of assuring that optical components, commonly very small in size, are completely sealed with no leakage such that the optical components are able operate under humid, dusty and harsh environment with long term reliability. In order to assure that the optical components are produced without leakage, leak tests of the optical components under high temperature and high humidity test chamber for long period of times over several thousand hours are typically performed. Optical performance parameters are then measured after the optical components are placed in a accelerated burn-in test in order to screen the defective devices with cycling under a high humidity condition over a burn-in testing period. These methods have several drawbacks. First of all, the test methods are time consuming and labor-intensive thus cause the production cost to increase significantly. Furthermore, these conventional test methods may not produce reliable test results for detecting the leaks. Depending on the size and position of the leak, changes in performance parameters of an optical component may or may not related to a leakage after the tests carried out in a test chamber. There are multiple reasons that could cause the changes in optical parameters. The tests and measurements provide no direct indications for detecting a leak. Additionally, the severe test conditions may be destructive to the optical components. The damages caused by the leakage tests may be unnecessary and could have been avoided if the leakage of the optical components can be detected by a less severe but more direct and sensitive testing method.

For these reasons, a need still exists in the art of optical component design, manufacture and testing to provide a new and improved component configuration and testing methods to conveniently detect the leakage of the optical component such that the difficulties and limitations can be resolved.

SUMMARY OF THE PRESENT INVENTION

It is therefore an object of the present invention to provide an improved method of manufacturing and testing the optical components such that a leak on an optical component can be more directly and conveniently detected to overcome the above mentioned difficulties and limitations encountered in the conventional test techniques.

Specifically, it is an object of the present invention to provide an improved method of component manufacturing and testing for the sealed fiber optical components by injecting a target gas with no optical interference effects into the sealed optical components. The sealed optical components are then placed in a leak detection chamber for measuring a variation of the amount of the target gas in the test chamber. A leak test is carried out by elevating the temperature in the test chamber thus causing the target gas in the optical components to expand and expelled from the sealed components if there is a leak. A simple and direct measurement is now provided for detecting a leak without testing the optical components for measuring performance parameters through many indirect and often unnecessary duty cycles of temperature cycling under high humidity pressure or other kinds of testing conditions.

Another object of the present invention is to provide a simple, direct and convenient method for manufacturing and testing fiber optical components to simplify the leak detection processes such that cost savings in component productions can be achieved and meanwhile component reliability can be improved.

Briefly, in a preferred embodiment, the present invention discloses a method for detecting a leak from a sealed optical device. The method includes the steps of a) injecting a target gas with no performance interference to the sealed optical device for leak detection followed by sealing the sealed optical device as usual. B) Placing the sealed device in a leak testing chamber and measuring a background level of the target gas in the leak-testing chamber. C) Heating the sealed device to a gas-expelling temperature for expelling the target gas from the leak in the sealed optical device. And D) detecting the target gas with a detection sensitivity in a one-part-per million (PPM) range in the leak-detecting chamber for comparing with the background level of the target gas for determining the leak in the sealed optical device. In a preferred embodiment, the target gas injected into the optical component may be a target gas of carbon dioxide or other non-hazardous gases. In another preferred embodiment, the step of heating the seated device is a step of heating the optical device to a temperature approximately between eighty to one hundred degrees Celsius.

In summary, this invention also discloses a sealed device that includes a sealed inner space containing a target gas useful for leakage detection. In a preferred embodiment, the sealed inner space containing a higher than a normal atmospheric content of the target gas. In a preferred embodiment, the sealed device is a sealed optical device. In another preferred embodiment, the sealed inner space of the sealed optical device containing a target gas of carbon dioxide or other non-hazardous gases.

These and other objects and advantages of the present invention will no doubt become obvious to those of ordinary skill in the art after having read the following detailed description of the preferred embodiment which is illustrated in the various drawing figures.

DETAILED DESCRIPTION OF THE INVENTION

Figure 1:
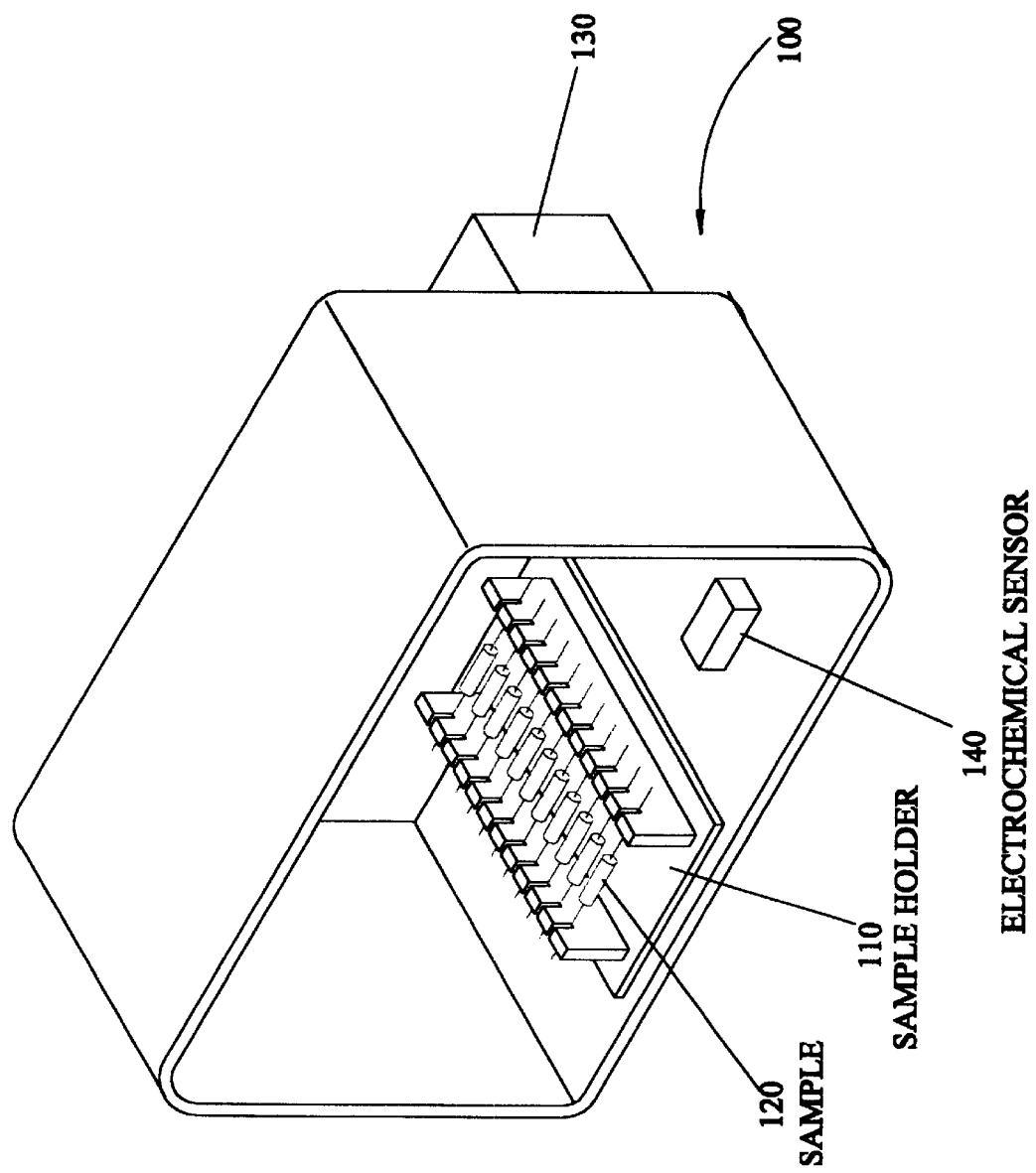
FIG. 1 is a perspective view of a leak test chamber of this invention with a sensor for detecting expelled target gas from a sealed optical component.

Referring to FIG. 1 for a perspective view of a leak test chamber 100 of this invention. The leak test chamber includes a test-component holder 110 for holding a plurality of sealed test-components 120. Each of theses sealed test-components 120 has a sealed inner space containing target gas injected into the inner space as one step of the manufacturing processes. The test chamber 100 further includes a temperature controller 130 for controlling the temperature of the test chamber between a room temperature and approximately one hundred degrees Celsius. The test-chamber further includes a sensor 140 for sensing the target gas. For the purpose of carrying out a leak detection for detecting a leak on the sealed test-component 120, the sealed test components 120 are placed on the test-component holder 110. The door of the test chamber 100 is closed and a background test is performed at a room temperature to determine the background level of the target gas. Then the temperature controller 130 is employed to elevate the temperature to a testing temperature around 80 to 100 degrees Celsius to expel the target gas from the sealed test-components 120. The sensor 140 then detect if the level of the target gas remains substantially the same as the background level or there is an increased level of the target gas for determining if there is a leak from any of the sealed test components 120.

There are many kinds of non-hazardous gases that would be suitable for use as the target gas for injection into a sealed device and used for leak detection. These target gases may include ammonia, butane, chlorine, ethanol, ethylene, heptane, hexane, hydrogen, hydrogen sulfide, iso propyl alcohol, LPG, methane, nitrogen dioxide, ozone, propane, sulfur dioxide, toluene, General IAQ and VOC's. There are many types of electrochemical sensors for detection of these target gases. The detection of these target gases can be achieved with commercially available sensors. Specifically, a company Capteur Sensors provides sensors for a wide range of applications. The sensors are made as solid state sensors manufactured with semiconductor technologies. The target gases, sensors, and range of detection sensitivities are provided in an Internet web site www.capteur.co.uk/cgi-bin/view.p15 as listed in Table 1 on the last page of the Specification.

According to above descriptions, this invention discloses a method for detecting a leak from a sealed optical device. The method includes a step a) of injecting a target gas with no performance interference to the sealed optical device for leak detection followed by sealing the sealed optical device. The method further includes step b) of placing the sealed device in a leak testing chamber and measuring a background level of the target gas in the leak testing chamber. The method further includes step c) of heating the sealed device to a gas-expelling temperature for expelling the target gas from the leak in the sealed optical device. The method further includes step d) of detecting the target gas in a one-part-per million (PPM) range in the leak detecting chamber for an comparing with the background level of the target gas for determining the leak in the sealed optical device. In a preferred embodiment, the step a) of injecting a target gas into the sealed optical device is a step of injecting a carbon dioxide gas into the sealed optical device. In another preferred embodiment, the step c) of heating the sealed optical device to a gas-expelling temperature is a step of heating the sealed device to a gas-expelling temperature of about eighty to one-hundred degrees Celsius for expelling the carbon-dioxide gas from the leak in the sealed optical device. In another preferred embodiment, the step of d) detecting the target gas in a one-part-per million (PPM) range in the leak testing chamber is a step of employing a solid state sensor for detecting a target gas of carbon-dioxide for determining the leak in the sealed optical device. In another preferred embodiment, the step b) of measuring a background level of the target gas in the leak testing chamber further comprising a step of first evacuating the leak testing chamber to a evacuated chamber pressure before measuring the background level of the target gas.

Figure 2:
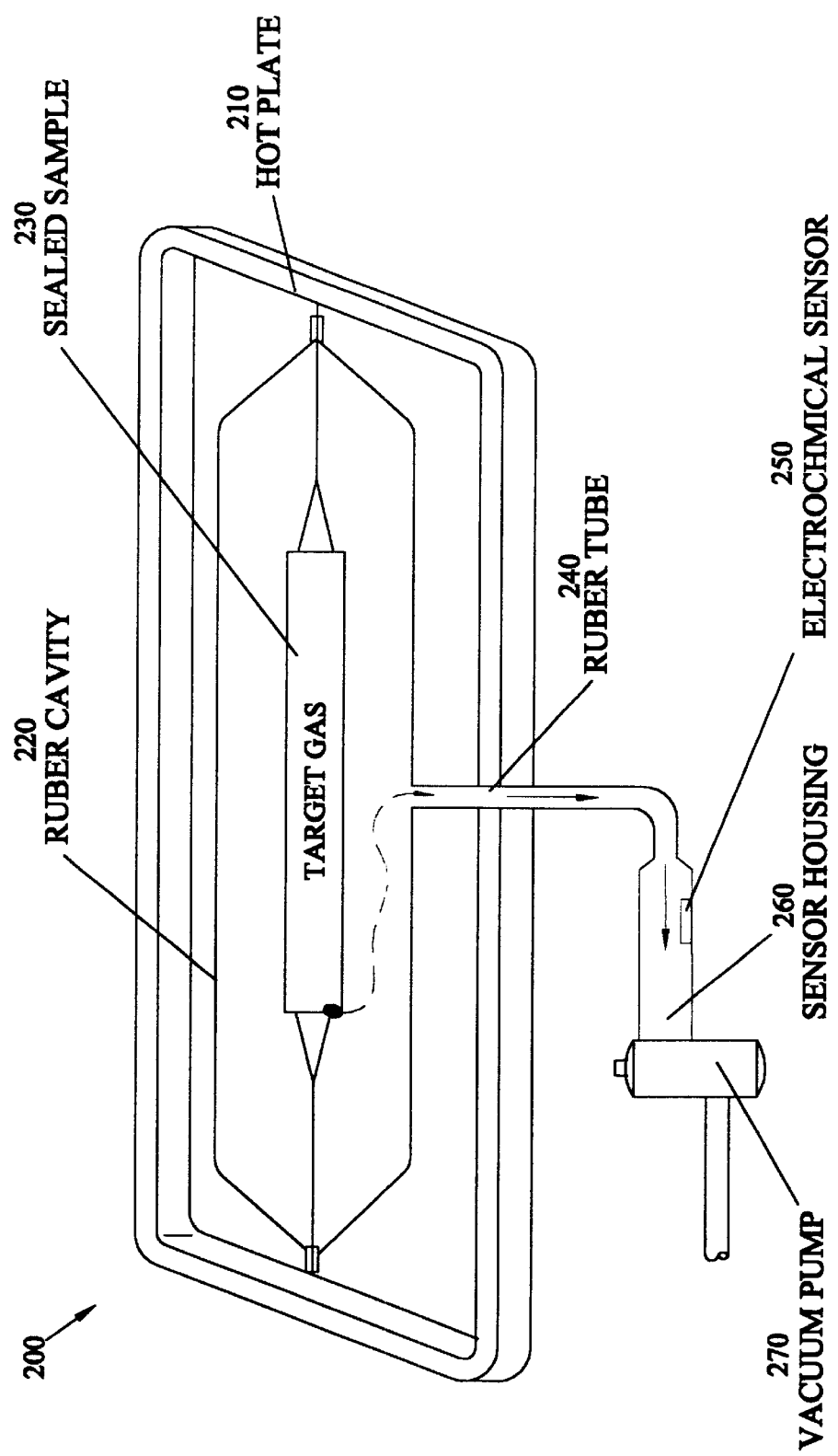
FIG. 2 is a functional block diagram of another preferred embodiment of a test chamber for detecting a leak from individual sealed optical component.

Referring to FIG. 2 for an alternate test chamber 200 of this invention. The test chamber 200 is supported on a heating plate 210 for heating the test chamber up to about 100 degrees Celsius. The test chamber 200 includes a rubber cavity 220 for placing a sealed test component 230. After the sealed test component 230 is placed in the rubber cavity, the test chamber also includes a top cover (not shown for clearly illustrating the placement of the test component), to cover the rubber cavity. A background level of target gas injected in the sealed test component 230 is first determined by drawing the air from the test chamber 200 inside the rubber cavity 220 through a rubber tube 240 to an electrochemical sensor 250. The rubber tube 240 has a first open end connected to and in atmospheric communication with the rubber cavity 220. A sensor housing 260 is attached at a second end of the rubber tube to support and contain the sensor 250. The air in the rubber cavity 220 is drawn by a vacuum pump 270 to flow from the rubber cavity 220 into the rubber tube 240 to pass through the electrochemical sensor 250. After a background level of target gas is determined, the test chamber is heated to an elevated temperature, e.g., 80–100 degrees Celsius, to determine if the test component 230 has a leak, e.g., leak 280. The target gas in the sealed test component 230 is expelled from the leak 280 and flow through the tube 240 to the detector 250 as illustrated by the dotted line. A leak-detection can be positively and definitively carried out to precisely determine if a specific individual sealed optical component has a leak.

Figure 3A:
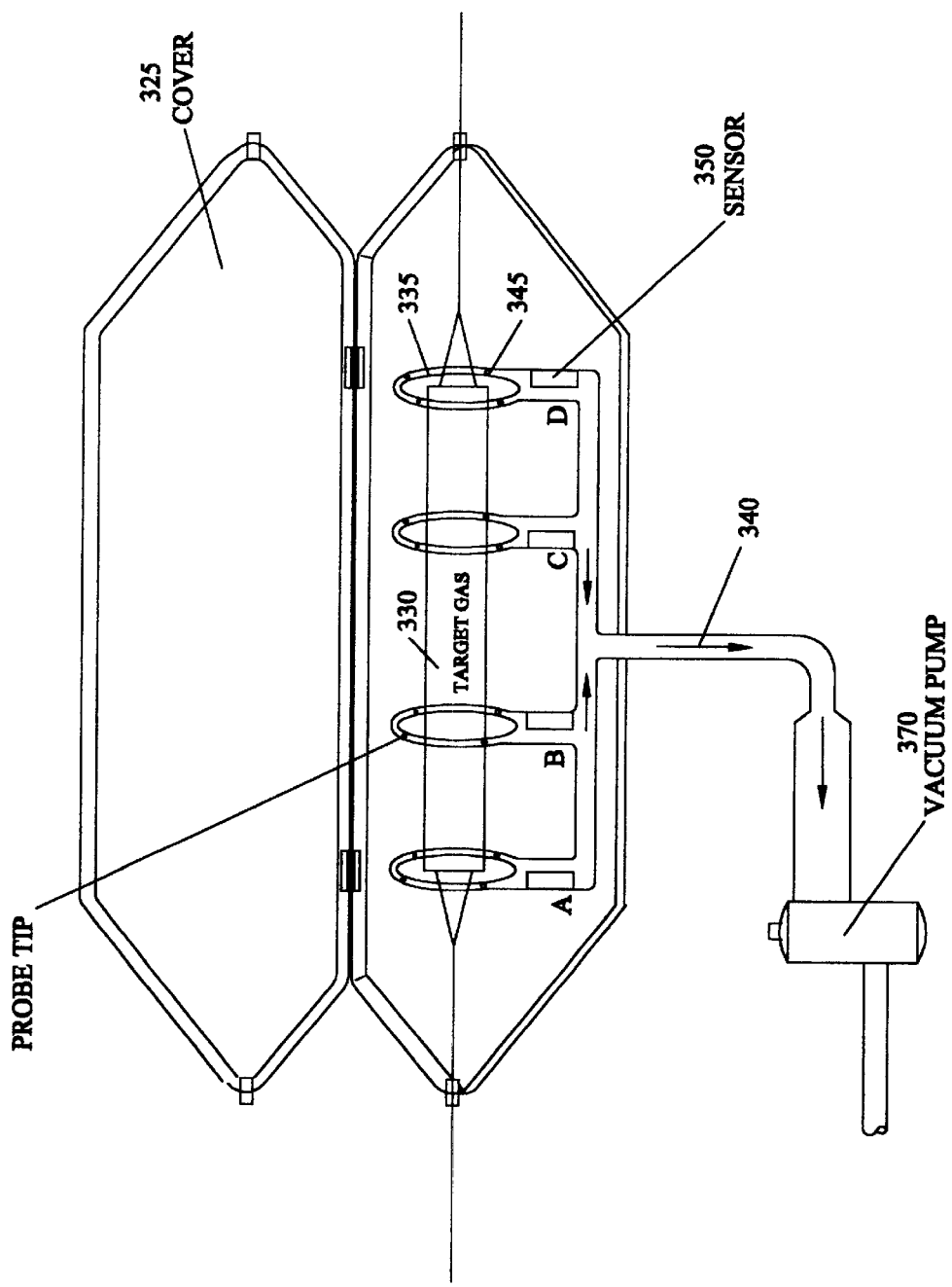
FIGS. 3A and 3B are respectively a functional block diagram and a perspective view of another preferred embodiment of a test chamber for detecting the location of a leak from an individual sealed optical component.
Figure 3B:
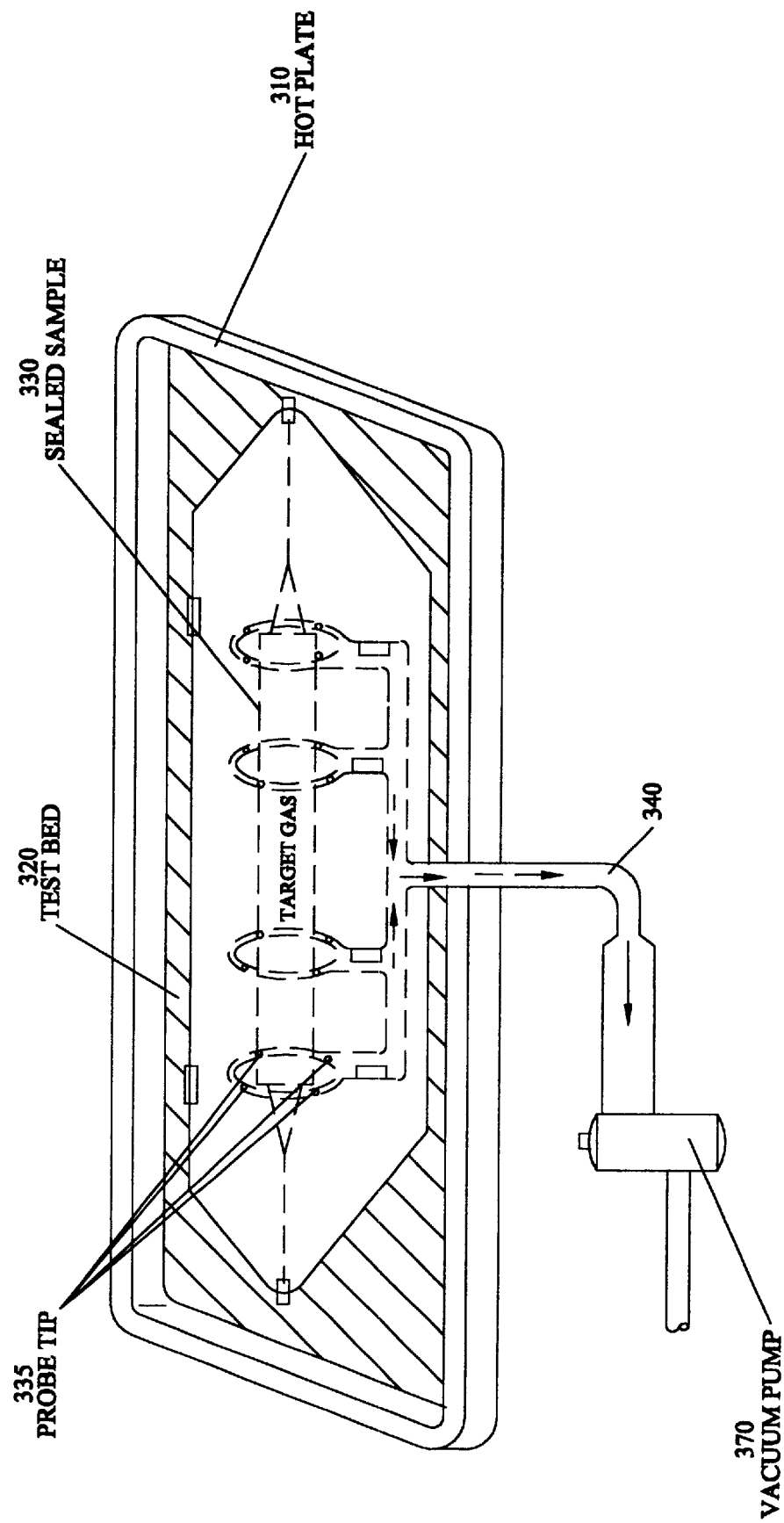

Referring to FIGS. 3A and 3B for another alternate test chamber 300 of this invention. The test chamber 300 is supported on a heating plate 310 for heating the test chamber up to about 100 degrees Celsius. The test chamber 300 includes a test bed 320 formed in a rubber cavity for placing a sealed test component 330. After the sealed test component 330 is placed in the test bed 320 in the rubber cavity, the test chamber also includes a top cover 325 to cover the rubber cavity. The test bed 320 includes several target gas sensing rings 335 and each sensing ring 335 has several air inlet 345 for drawing an airflow by a air-drawing force asserted by a vacuum pump 370 through a rubber tube 340. Each of these sensing rings 335 further has a target sensor 345 disposed in the manifold of the sensing ring for detecting trace of the target gas with a detection sensitivity in an rang of one part in-a-million. After the sealed component 330 is placed on the test bed 320 and the cover 325 is closed, the test chamber is heated to an elevated temperature, e.g., 80–100 degrees Celsius. The target gas in the sealed test component 330 is expelled from a leak and flow through the air inlets of the sensing rings 335 to the detector 350. A leak-detection can be positively and definitively carried out to precisely determine if a specific individual sealed optical component has a leak at a particular location. The sensing rings 335 are placed near the points of the sealed optical component 330 where the leak is most likely to occur. The test chamber 300 provides a special advantage for precise detect the location of a leak of a sealed optical component by providing target gas sensing at different positions along the longitudinal direction of the test device 330.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

TABLE 1

Sensor Index

| Gas | Range | Product Code |
|---|---|---|
| Sensor Utilisation Module | | SUM |
| Ammonia | 0–100 ppm | GS06 |
| Butane | 0–1% | CTS04 |
| Dual sensor CO/NOx | 0–5 ppm | GLG0710 |
| Carbon Monoxide | 0–400 ppm | NGL07 |
| Chlorine | 0–5 ppm | LGS09 |
| Ethanol | 0–1000 ppm | AAS14 |
| Ethylene | 0–1000 ppm | CTS11 |
| Heptane | 0–1000 ppm | CTS27 |
| Hexane | 0–1000 ppm | CTS19 |
| Hydrogen Leak Sensor | 0–1% | NGL23 |
| Hydrogen | 0–10000 ppm | CTS23 |
| Hydrogen Sulphide | 0–10 ppm | GS05 |
| Iso Propyl Alcohol | 0–200 ppm | AAS20 |
| LPG | 0–1% | CTS03 |
| Methane Gas Sensor | 0–1% | WL02 |
| Methanol | 0–1% | AAS13 |
| Nitrogen Dioxide | 0–5 ppm | LGS10 |
| Ozone | 0–300 ppb | LGL52 |
| Propane | 0–1% | CTS03 |
| Sulphur Dioxide | 1–10 ppm | GS22 |
| Toluene | 0–500 ppm | AAS25 |
| VOCs | 0–10 ppm | GSV/M/H |

What is claimed is:

1. A method for detecting a leak from a sealed optical device comprising:

injecting a target gas with no performance interference to said sealed optical device for leak detection followed by sealing said sealed optical device;

placing said sealed device in a leak testing chamber and measuring a background level of said target gas in said leak testing chamber;

heating said sealed device to a gas-expelling temperature for expelling said target gas from said leak in said sealed optical device; and detecting said target gas in a one-part-per million (PPM) range in said leak detecting chamber for an comparing with said background level of said target gas for determining said leak in said sealed optical device.

2. The method for detecting a leak of claim 1 wherein:
said step of injecting a target gas into said sealed optical device is a step of injecting a carbon dioxide gas into said sealed optical device.

3. The method for detecting a leak of claim 2 wherein:
said step of heating said sealed optical device to a gas-expelling temperature is a step of heating said sealed device to a gas-expelling temperature of about eighty to one-hundred degrees Celsius for expelling said carbon-dioxide gas from said leak in said sealed optical device.

4. The method for detecting a leak of claim 1 wherein:
said step of detecting said target gas in a one-part-per million (PPM) range in said leak testing chamber is a step of employing a solid state sensor for detecting a target gas of carbon-dioxide for determining said leak in said sealed optical device.

5. The method for detecting a leak of claim 1 wherein:
said step of measuring a background level of said target gas in said leak testing chamber further comprising a step of first evacuating said leak testing chamber to a evacuated chamber pressure before measuring said background level of said target gas.

6. A method for detecting a leak from a sealed device comprising:

injecting a target gas for leak detection followed by sealing said sealed device;

placing said sealed device in a leak testing chamber;

heating said sealed device to a gas-expelling temperature for expelling said target gas from said leak in said sealed device; and detecting said target gas expelled from said sealed device for determining said leak in said sealed device.

7. The method for detecting a leak of claim 6 wherein:
said step of injecting a target gas for leak detection followed by sealing said sealed device is a step of injecting a non-hazardous target gas into an optical device followed by sealing said optical device into a sealed optical device.

8. The method for detecting a leak of claim 6 wherein:
said step of injecting a target gas for leak detection followed by sealing said sealed device is a step of injecting a target gas with no performance interference to said sealed device whereby said target gas remains in said sealed device after a leakage test.

9. The method for detecting a leak of claim 7 wherein:
said step of injecting a target gas into said sealed optical device is a step of injecting a carbon dioxide gas into said sealed optical device.

10. The method for detecting a leak of claim 6 wherein:
said step of placing said sealed device in a leak testing chamber further comprising a step of measuring a background level of said target gas before heating said sealed device to a gas-expelling temperature.

11. The method for detecting a leak of claim 9 wherein:
said step of heating said sealed device to a gas-expelling temperature is a step of heating said sealed device to a gas-expelling temperature of about eighty to one-hundred degrees Celsius for expelling said carbon-dioxide gas from said leak in said sealed optical device.

12. The method for detecting a leak of claim 6 wherein:
said step of detecting said target gas in said leak detecting chamber is a step of detecting said target gas in a one-part-per million (PPM) range expelled from said sealed device for determining said leak in said sealed device.

13. The method for detecting a leak of claim 6 wherein:
said step of detecting said target gas expelled from said sealed device for determining said leak in said sealed device is a step of applying an air-drawing pressure around said sealed device for drawing said target gas expelled from said sealed device to pass through a target gas sensor for detecting said target gas expelled from said sealed device.

14. The method for detecting a leak of claim 12 wherein:
said step of detecting said target gas in a one-part-per million (PPM) range in said leak testing chamber is a step of employing a solid state sensor for detecting a target gas of carbon-dioxide for determining said leak in said sealed device.

15. The method for detecting a leak of claim 7 wherein:
said step of injecting a target gas into an optical device is a step of injecting a target gas into a fiber optical collimator followed by sealing said optical device into a sealed optical device.

16. The method for detecting a leak of claim 7 wherein:
said step of injecting a target gas into an optical device is a step of injecting a target gas into a fiber optical coupler followed by sealing said optical device into a sealed optical device.

17. The method for detecting a leak of claim 7 wherein:
said step of injecting a target gas into an optical device is a step of injecting a target gas into a fiber optical isolator followed by sealing said optical device into a sealed optical device.

18. The method for detecting a leak of claim 13 wherein:
said step of applying an air-drawing pressure around said sealed device for drawing said target gas expelled from said sealed device further includes a step of applying an air-drawing pressure around different sections of said sealed device for drawing said target gas expelled from said different sections of said sealed device for detecting said target gas expelled from each of said different sections of said sealed device.

19. An apparatus for detecting a leak from a sealed optical device comprising:
a leak testing chamber for placing a sealed optical device therein the sealed optical device sealed and including a target gas sealed therein with no performance interference to said sealed optical devices; means for measuring a background level of said target gas in said leak test chamber;
a heating means for heating said sealed optical device to a gas-expelling temperature for expelling said target gas from a leak if present in said sealed optical device; and
a target gas sensor for detecting said target gas expelled from said sealed optical device and means for comparing said background level with said expelled target gas for determining said leak in said sealed device.

20. The apparatus for detecting a leak of claim 19 wherein:
said target gas sensor is a gas sensor for detecting a non-hazardous target gas.

21. The apparatus for detecting a leak of claim 19 wherein:
said target gas sensor is a gas sensor for detecting a carbon dioxide target gas with no performance interference to said sealed optical device.

22. The apparatus for detecting a leak of claim 21 wherein:
said heating means for heating said sealed optical device to a gas-expelling temperature is provided for heating said sealed optical device to a gas-expelling temperature of about eighty to one-hundred degrees Celsius for expelling said carbon-dioxide gas from said leak in said sealed optical device.

23. The apparatus for detecting a leak of claim 19 wherein:
said target gas sensor for detecting said target gas around said sealed optical device is a target gas sensor for detecting said target gas in a one-part-per million (PPM) range expelled from said sealed optical device for determining said leak in said sealed optical device.

24. The apparatus for detecting a leak of claim 19 further comprising:
an air-drawing means for applying an air-drawing pressure around said sealed optical device for drawing said target gas expelled from said sealed optical device to pass through said target gas sensor for detecting said target gas expelled from said sealed optical device.

25. The apparatus for detecting a leak of claim 19 wherein:
said target gas sensor for detecting said target gas expelled from said sealed optical device is a solid state gas sensor.

26. The apparatus for detecting a leak of claim 19 further comprising:
an air-drawing means for applying an air-drawing pressure around said sealed optical device for drawing said target gas expelled from different sections of said sealed optical device for detecting said target gas expelled from each of said different sections of said sealed optical device.

* * * * *

UNITED STATES PATENT AND TRADEMARK OFFICE
CERTIFICATE OF CORRECTION

PATENT NO.   : 6,696,296 B2
DATED        : February 24, 2004
INVENTOR(S)  : Li et al.

It is certified that error appears in the above-identified patent and that said Letters Patent is hereby corrected as shown below:

<u>Title page</u>,
Insert Item:
-- [*] Notice: Subject to any disclaimer, the term of this patent is extended or adjusted under 35 U.S.C. 154 (b) 512 days. --.

Signed and Sealed this

Tenth Day of January, 2006

JON W. DUDAS
*Director of the United States Patent and Trademark Office*